United States Patent [19]

Spencer

[11] 4,301,158
[45] Nov. 17, 1981

[54] N-(2-PROPYNYL)-2,6-DINITRO-BENZENAMINE DERIVATIVES

[75] Inventor: Homer K. Spencer, Randolph, N.J.

[73] Assignee: Sandoz, Inc., East Hanover, N.J.

[21] Appl. No.: 139,435

[22] Filed: Apr. 11, 1980

[51] Int. Cl.³ .................... A01N 41/06; A01N 37/34; A01N 33/18; C07C 87/00
[52] U.S. Cl. ............................ 424/228; 260/397.7 R; 260/465 E; 424/304; 424/330; 564/441
[58] Field of Search .................... 564/441; 260/465 E, 260/397.7 R; 424/228, 304, 330

[56] References Cited

U.S. PATENT DOCUMENTS 3,257,190  6/1966  Soper .............................. 564/441 X
4,065,559 12/1977  Froyd ................................ 424/229

FOREIGN PATENT DOCUMENTS 2161879  6/1973  Fed. Rep. of Germany .

Primary Examiner—Dolph H. Torrence

Attorney, Agent, or Firm—Gerald D. Sharkin; Richard E. Vila

[57] ABSTRACT

Fungicides are of the formula:

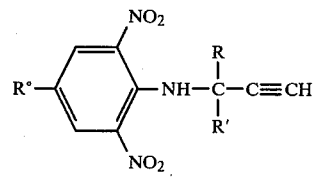

wherein
R and R' are each independently alkyl of 1 to 4 carbon atoms,
R° is trihalomethyl in which the halo atoms are of atomic weight of from 18 to 36, e.g. trifluoromethyl or trichloromethyl, cyano or —SO$_2$NR"R"', and
R" and R"' are each independently hydrogen or alkyl of 1 to 4 carbon atoms.

15 Claims, No Drawings

N-(2-PROPYNYL)-2,6-DINITRO-BENZENAMINE DERIVATIVES

The present invention relates N-(2-propynyl)-2,6-dinitro-benzenamines and derivatives thereof, their use as fungicides and agricultural compositions for facilitating such use.

The compounds of the present invention may be represented structurally by the following formula I:

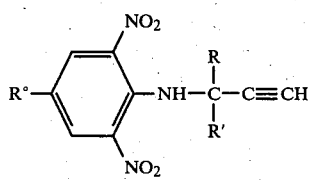

wherein
R and R' are each independently alkyl of 1 to 4 carbon atoms,
R° is trihalomethyl in which the halo atoms are of atomic weight of from 18 to 36, e.g. trifluoromethyl or trichloromethyl, cyano or $-SO_2NR''R'''$, and,
R'' and R''' are each independently hydrogen or alkyl of 1 to 4 carbon atoms.

The compounds of the formula I may be conveniently prepared by reacting a compound of the formula II:

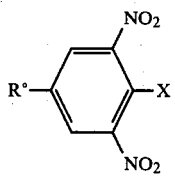

wherein X is chloro or bromo and R° is as above defined, with a compound of the formula III:

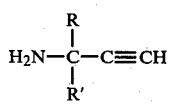

wherein R and R' are as above defined:

The preparation of compounds I by the reaction of a compound II with a compound III may be carried out at temperatures of from 0° C. to 100° C., preferably 15° C. to 35° C., and in an inert solvent which may be any of the several conventional types such as the lower alkanols, e.g. ethanol. The reaction is desirably carried out in the presence of a base or acid binding agent which may also be any of the several conventional types useful for facilitating such reactions, e.g. a tertiary amine such as triethylamine or pyridine. The reaction product of the formula I may be separated and recovered from the reaction mixture in which it is formed by working up by established procedures.

Many of the compounds of each formulae II and III are known and those which are not known per se may be prepared from known materials by procedures analogous to those known for preparation of the known compounds.

The compounds of the formula I are useful as fungicides in combatting phytopathogenic fungus, including particularly smuts and those of the genus Rhizoctonia, as indicated by standard in vitro and in vivo tests of the type hereinafter illustrated. For such use the compounds of the formula I may be applied to plants, seed or soil in a manner conventional in the use of fungicidal agents. As will be appreciated, the amount of the compound of the formula I to be applied will vary depending upon known factors such as the particular compound employed, whether the treatment is prophylactic or therapeutic, whether the compound is applied as a foliar spray, a soil treatment or a seed dressing, the species of fungus under treatment and the time of application. However, in general, satisfactory results are obtained when the compound is applied to a crop locus, either on crops or to soil, at a rate of from about 0.1 to 10, preferably about 0.5 to 5 kg (active ingredient)/hectare. The treatment may be repeated as required, e.g. at 8 to 30 day intervals. When employed as a seed dressing, satisfactory results are obtained when the compound is employed at a rate of from about 0.01 to 0.5, preferably about 0.02 to 0.2 kg/100 kg seed. Application to the soil is generally preferred.

The term "soil" as used herein is intended to embrace any conventional growing medium whether natural or artificial.

The invention also provides, as an additional feature, fungicidal compositions, comprising, as fungicide, a compound of formula I and an inert fungicide carrier. In general, such compositions contain from about 0.01 to 90, preferably from about 0.1 to 60% by weight of active agent. They may be in concentrate form, for dilution down prior to application, or in dilute, ready to apply, form. As examples of particular forms may be given wettable powder, emulsion concentrate, dusting, spraying, granulate and delayed release forms, incorporating conventional carriers and such other diluents and/or adjuvants conventional in the agricultural art. Application forms of those compositions generally contain between about 0.01 and 10% by weight of a compound of formula I as active agent. Concentrate forms of compositions for fungicide use generally contain between about 2 and 80%, preferably between about 5 and 70%, by weight of a compound of formula I as active agent. Emulsion concentrate forms generally contain from about 10 to 70%, preferably about 20 to 60% by weight of active ingredient. Solid, particulate compositions are preferred.

The compositions particularly adapted for spraying preferably include a surfactant such as a liquid polyglycol ether, a fatty alkyl sulphate or a lignin sulphonate.

In addition to conventional carrier and surface-active materials, formulations of the compound I of the invention may also contain further additives with special purposes e.g. stabilizers, deactivators (for solid formulations on carriers with an active surface), agents for improving the adhesion to plants, corrosion inhibitors, anit-foaming agents and colorants.

Moreover, further fungicides, bacteriacides or other beneficially-acting materials, such as insecticides, may be present in the formulations and are contemplated as further embodiments of this invention.

Examples of the production of fungicide formulations are as follows:

(a) Wettable powder formulation 50 parts of N-(1,1-dimethyl-2-propynyl)-2,6-dinitro-4-(trifluoromethyl)benenamine are ground with 2 parts of lauryl sulphate, 3 parts sodium lignin sulphonate and 45 parts of finely divided kaolinite until the mean particle size is below 5 microns. The resulting wettable powder so obtained is diluted with water before use to a concentration of between 0.01% to 5% active agent. The resulting spray liquor may be applied by foliar spray as well as by root drench application.

(b) Granulate formulation

Onto 94.5 parts by weight of quartz sand in a tumbler mixer is sprayed 0.5 parts by weight of a binder (non-ionic tenside) and the whole thoroughly mixed. 5 parts by weight of powdered N-(1,1-dimethyl-2-propynyl)-2,6-dinitro-4-(trifluoromethyl)benzenamine are then added and thorough mixing continued to obtain a granulate formulation with a particle size in the range of from 0.3 to 0.7 mm. The granulate may be applied by incorporation into the soil adjacent the plants to be treated.

(c) Emulsion Concentrate 25 parts by weight of N-(1,1-dimethyl-2-propynyl)-2,6-dinitro-4-(trifluoromethyl)benzenamine are mixed with 30 parts by weight of iso-octyl phenyl octaglycol ether and 45 parts by weight of a petroleum fraction with a boiling range of 210°–280° C. ($D_{20}$:0.92). The concentrate is diluted with water to the desired concentration.

(d) Seed dressing 45 parts of a compound of N-(1,1-dimethyl-2-propynyl)-2,6-dinitro-4-(trifluoromethyl)benzenamine are mixed with 1.5 parts of diamylphenoldecaglycolether ethylene oxide adduct, 2 parts of spindle oil, 51 parts of fine talcum and 0.5 parts of colorant rhodamin B. The mixture is ground in a contraplex mill at 10,000 rpm until an average particle size of less than 20 mincrons is obtained. The resulting dry seed dressing powder has good adherance and may be applied to seeds, e.g. by mixing for 2 to 5 minutes in a slowly turning vessel.

The following tests are illustrative of the manner by which the fungicidal activity of the compounds of the formula I may be indicated. Where indicated below, the fungi employed are those species identified by strain number in the following table A.

TABLE A

| Strain-No. | SPECIES AND STRAINS USED Name | isolated from |
|---|---|---|
| 30 | Rhizoctonia solani | cotton |
| 67 | Rhizoctonia solani | potato |
| 84 | Rhizoctonia solani | " |
| 104 | Rhizoctonia solani | " |
| 110 | Rhizoctonia sp. | sugar beet |
| 111 | Rhizoctonia sp. | " |
| 122 | Rhizoctonia sp. | oat |
| 126 | Ustilago maydis (maintained in conidial) (state) | corn |

TEST METHOD A: In vitro; different concentrations (ppm) of the active ingredient are incorporated in malt agar plates which are then innoculated by spraying with a spore suspension of the fungus or by placing an agar plug containing the fungus in the center of the plate. The plates are then incubated at room temperature for 2–5 days and the efficacy of the tested compounds in inhibiting mycelial growth determined by comparing the growth of the fungus with that in untreated, similarly inoculated and incubated plates. The results in Tables 1a and 1b below compare the compound of Example 1 hereinafter with several known fungicides by a determination of their $ED_{50}$ and $ED_{90}$ values.

TABLE 1a $ED_{50}$ (ppm necessary to inhibit mycelial growth by 50%)

| Prep. | Strain no. | | | | | | | |
|---|---|---|---|---|---|---|---|---|
| | 30 | 67 | 84 | 104 | 110 | 111 | 122 | 126 |
| VITAVAX | 0.45 | 0.47 | 0.07 | 0.87 | 0.43 | 0.02 | 2.21 | 0.25 |
| CALIRUS | 2.07 | 0.43 | 1.25 | 0.60 | 2.65 | 0.90 | 1.71 | 5.71 |
| PCNB | 40.20 | 15.6 | 200 | 5.22 | 470 | >200 | 9.01 | 5.15 |
| THIOTOX | 7.7 | 8.12 | 5.55 | 1.88 | 10.13 | 1.96 | 3.12 | 1.56 |
| MANCOZEB | 19.3 | 4.74 | 5.99 | 3.90 | 22.43 | 5.44 | 7.34 | 5.71 |
| DEMOSAN | 1.88 | 1.68 | 8.01 | 0.15 | 6.04 | 1.44 | 10.6 | 7.87 |
| BENLATE | 1.24 | 2.07 | 1.93 | 1.65 | 2.84 | 0.29 | 1.65 | 0.77 |
| compound of Example 1 | 0.39 | <0.2 | 0.41 | <0.2 | <0.2 | 2.37 | 0.33 | 0.48 |

TABLE 1b $ED_{90}$ (ppm necessary to inhibit mycelial growth by 90%)

| Prep. | Strain no. | | | | | | | |
|---|---|---|---|---|---|---|---|---|
| | 30 | 67 | 84 | 104 | 110 | 111 | 122 | 126 |
| VITAVAX | 166 | 13580 | 38 | 1620 | 36 | 33 | 570 | 3 |
| CALIRUS | 16 | 5 | 9 | 4 | 22 | 6 | 9 | 17 |
| PCNB | 253 | 946 | 388 | 809 | 2250 | >12000 | >10000 | 17 |
| THIOTOX | 117 | 48 | 19 | 9 | 82 | 113 | 69 | 8 |
| MANCOZEB | 283 | 41 | 28 | 28 | 94 | 225 | 125 | 17 |
| DEMOSAN | 9 | 19 | 24 | 8 | 38 | 40 | 4170 | 24 |
| BENLATE | 6 | 14 | 8 | 7 | 16 | 7 | 35 | 5 |
| compound of Example 1 | 4 | 1 | 4 | <0.2 | <0.2 | 40 | 12 | 4 |

TEST AP-2

TEST METHOD B: In vivo simulation of fumigation effect against Rhizoctonia solani in soil; oat-corns are autoclaved in malt water and then inoculated with Rhizoctonia solani (strain No. 30). After 10 days the resulting colonized oat corns are harvested and carefully dried. A steamed mixture of peat and sand (3:1 by volume) is treated with the active ingredient at different concentrations (ppm) and then the oat corns are buried in the treated peat/sand mixture. After incubation for 1,2,4 or 8 days at 25° C., the oat corns are placed on malt agar and the resulting mycelium measured after 24 hours. An average of 75 oat corns are used in each evaluation. The results in Table 2 below compare the compound of Example 1 hereinafter with certain known fungicides.

TABLE 2

Activity against *Rhizoctonia solani* in a simulated fumigation test

| Compound | mg a.i./ lit. soil (=ppm) | % inhibition of mycelial growth[1] after x days of burial of corns | | | |
|---|---|---|---|---|---|
| | | 1 day | 2 days | 4 days | 8 days |
| compound of Example 1 | 160 | 100 | 100 | 95 | 95 |
| | 40 | 45 | 30 | 40 | 45 |
| | 10 | 0 | 5 | 0 | 0 |
| Benlate | 160 | 25 | 55 | 75 | 90 |
| | 40 | 10 | 10 | 25 | 15 |
| | 10 | 5 | 0 | 0 | 0 |
| Vitavax | 160 | 75 | 90 | 70 | 80 |
| | 40 | 40 | 75 | 60 | 0 |
| | 10 | 0 | 20 | 0 | 0 |
| Demosan | 160 | 45 | 55 | 65 | 75 |
| | 40 | 0 | 25 | 15 | 0 |
| | 10 | 0 | 5 | 5 | 0 |

[1] Radial growth of check: 11.8–14.4 mm

TEST AP-3

TEST METHOD C: In vivo; dip treatment of Rhizoctonia infected oat corns. Oat corns are inoculated as described in Test AP-2, above, and, after drying, are dipped for 30 minutes into a solution of the active ingredient. After drying for 24 hours, the treated oat corns are placed on malt agar and allowed to incubate for 24 hours at 25° C. The radial mycelial growth is then measured. The results in Table 3 below compare the compound of Example 1 hereinafter with various known fungicides at various concentrations (ppm) of active ingredient in the dipping solutions.

TABLE 3

Effectiveness of dip treatment against *Rhizoctonia solani* on oat corns

| Compound | % oat corns without mycelial outgrowth Conc. of dipping solution (ppm a.i.) | | | | | | | |
|---|---|---|---|---|---|---|---|---|
| | 2000 | 500 | 125 | 32 | 8 | 2 | ED$_{50}$ | ED$_{100}$ |
| compound of Example 1 | 100 | 100 | 70 | 15 | 0 | 0 | 79 | 235 |
| Vitavax | 7 | 0 | 0 | 0 | 0 | 0 | >2000 | — |
| Demosan | 80 | 7 | 0 | 0 | 0 | 0 | 1196 | 2830 |
| Calirus | 40 | 0 | 0 | 0 | 0 | 0 | >2000 | — |
| PCNB | 0 | 0 | 0 | 0 | 0 | 0 | >2000 | — |
| Benlate | 0 | 0 | 0 | 0 | 0 | 0 | >2000 | — |

TABLE 3-continued

Effectiveness of dip treatment against *Rhizoctonia solani* on oat corns

| TMTD | 0 | 0 | 0 | 0 | 0 | 0 | >2000 | — |
|---|---|---|---|---|---|---|---|---|
| Mancozeb | 0 | 0 | 0 | 0 | 0 | 0 | >2000 | — |

| | % inhibition of mycelial growth of developing colonies | | | | | | | |
|---|---|---|---|---|---|---|---|---|
| compound of Example 1 | 100 | 100 | 99 | 95 | 80 | 65 | 0.88 | 17.5 |
| Vitavax | 90 | 85 | 75 | 50 | 15 | 5 | 46 | 957 |
| Demosan | 99 | 75 | 40 | 15 | 10 | 0 | 167 | 1412 |
| Calirus | 90 | 70 | 45 | 30 | 15 | 5 | 130 | 3150 |
| PCNB | 90 | 70 | 15 | 5 | 10 | 0 | 262 | 4455 |
| Benlate | 60 | 30 | 10 | 10 | 0 | 0 | 1435 | — |
| TMTD | 30 | 15 | 10 | 10 | 5 | 5 | >2000 | — |
| Mancozeb | 10 | 0 | 0 | 5 | 0 | 0 | >2000 | — |

TEST AP-4

TEST METHOD D: In vivo; fungicidal activity against *Rhizoctonia solani* on sugar beets. Sugar beet seeds are planted in pots containing soil which constitutes a mixture of peat and sand (3:1 by volume) and which has been infested with *Rhizoctonia solani* (strain No. 110). The pots are then incubated using different temperatures for different sets of pots. The results in Table 4 below compare the compound of Example 1 hereinafter with certain known fungicides at different incubation temperatures and at different concentrations of active ingredient in the soil.

TABLE 4

Fungicidal activity in soil against *Rhizoctonia solani* on sugar beets

| Compound | mg a.i. per lit soil | % fung. activity | | | emergence | | |
|---|---|---|---|---|---|---|---|
| | | 15° C. | 18° C. | 25° C. | 15° C. | 18° C. | 25° C. |
| Check Inoculated | — | (100) | (100) | (100) | 90 | 90 | 60 |
| Check | — | (0) | (0) | (0) | 50 | 50 | 0 |
| Compound of Example 1 | 20 | 100 | 80 | 100 | 100 | 70 | 80 |
| | 10 | 100 | 95 | 100 | 100 | 80 | 80 |
| | 5 | 100 | 95 | 100 | 100 | 80 | 70 |
| | 2.5 | 35 | 55 | 30 | 70 | 60 | 20 |
| | 1.3 | 90 | 50 | 0 | 90 | 60 | 0 |
| Vitavax | 20 | 100 | 90 | 100 | 90 | 80 | 60 |
| | 10 | 100 | 70 | 80 | 90 | 70 | 50 |
| | 5 | 85 | 80 | 15 | 80 | 80 | 10 |
| | 2.5 | 100 | 70 | 0 | 100 | 70 | 0 |
| | 1.3 | 25 | 15 | 0 | 60 | 40 | 0 |
| Benlate | 20 | 100 | 95 | 100 | 90 | 80 | 80 |
| | 10 | 80 | 65 | 65 | 80 | 70 | 40 |
| | 5 | 55 | 10 | 5 | 70 | 30 | 0 |
| | 2.5 | 35 | 20 | 0 | 70 | 40 | 0 |
| | 1.3 | 0 | 0 | 0 | 50 | 30 | 0 |

The compounds of the formula I are therefore especially useful in combatting fungi of the genus Rhizoctonia in plants such as, for example, cereals, sugar beet, soybeans, peanuts, cotton and potato, e.g. *Rhiz. Solani* in cotton and other crops, and in combatting fungi of the order Ustilagenales such as those of the genus Ustilago in plants such as barley, wheat, corn and sugarcane, e.g. *U. maydis* on corn and *U. nuda*.

The generally preferred compounds of the formula I are those having one or both of the following features:
(a) R and R' each independently being alkyl of 1 or 2 carbon atoms and particularly both being methyl; and
(b) R° being trihalomethyl or cyano, more preferably trifluoromethyl.

The following examples demonstrating particular compounds I and their preparation are given for purposes of illustration only.

EXAMPLE 1

N-(1,1-dimethyl-2-propynyl)-2,6-dinitro-4-(trifluoromethyl)benzenamine

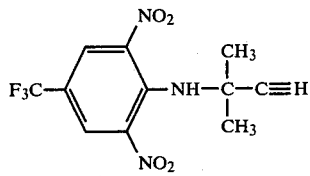

A solution of 12.0 g. of 1,1-dimethylpropargylamine in 50 ml. of ethanol is dried over anhydrous sodium sulfate and celite, and then added dropwise with stirring at room temperature to a solution of 35.1 g. of 4-chloro-3,5-dinitrobenzotrifluoride and 16.3 g. of triethylamine in 150 ml. of ethanol. The resulting solution is stirred for 3 days at room temperature and treated by addition of 100 ml. of water. The resulting yellow solid is recovered by filtering, dried and recrystallized from toluene/hexane (1:1) to obtain N-(1,1-dimethyl-2-propynl)-2,6-dinitro-4-(trifluoromethyl)benzenamine, m.p. 55°–58° C.

EXAMPLE 2

Following the procedure of Example 1 the following additional compound of the invention is prepared:

(A) N-(1,1-dimethyl-2-propynyl)-2,6-dinitro-4-(cyano)benzenamine, m.p. 100°–150° C.

This compound (of Example 2A) also shows strong fungicidal activity in the above-described tests.

What is claimed is:

1. A compound of the formula:

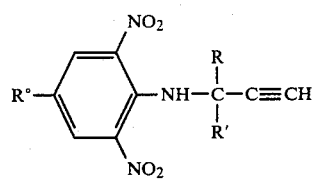

wherein
R and R' are each independently alkyl of 1 to 4 carbon atoms,
R° is trihalomethyl in which the halo atoms are of atomic weight of from 18 to 36, cyano or $-SO_2NR''R'''$, and
R'' and R''' are each independently hydrogen or alkyl of 1 to 4 carbon atoms, and 2. A compound of claim 1 in which R° is trihalomethyl or cyano.

3. A compound of claim 2 in which R° is trifluoromethyl.

4. A compound of claim 1, 2 or 3 in which each of R and R' are independently methyl or ethyl.

5. The compound of claim 1 in which R° is trifluoromethyl and R and R' are each methyl.

6. A fungicidal composition comprising an inert agriculturally acceptable carrier and a fungicidally effective amount of a compound of claim 1.

7. A composition of claim 6 in which the carrier is a solid carrier.

8. A composition of claim 6 or 7 in which the compound is the compound in which R° is trifluoromethyl and R and R' are each methyl.

9. The method of combatting phytopathogenic fungus in a plant locus comprising applying to said locus a fungicidally effective amount of a compound of claim 1.

10. The method of claim 9 in which the compound is a compound in which R° is trihalomethyl or cyano.

11. The method of claim 10 in which the compound is a compound in which R° is trifluoromethyl.

12. The method of claim 11 in which the compound is a compound in which R and R' are independently methyl or ethyl.

13. The method of claim 12 in which the compound is the compound in which R° is trifluoromethyl and R and R' are each methyl.

14. The method of claim 9, 10, 11, 12 or 13 in which the fungus combatted is of the order Ustilagenales or of the genus Rhizoctonia.

15. The method of claim 14 in which the compound is applied to the soil of the plant locus.

* * * * *